United States Patent [19]

McCaffrey et al.

[11] Patent Number: 4,460,476

[45] Date of Patent: Jul. 17, 1984

[54] TREATMENT OF ORGANICS CONTAINING WATER

[75] Inventors: David J. A. McCaffrey, Cheltenham; William D. Jones, Tewkesbury, both of England

[73] Assignee: Coal Industry (Patents) Limited, London, England

[21] Appl. No.: 519,887

[22] Filed: Aug. 3, 1983

Related U.S. Application Data

[63] Continuation of Ser. No. 325,902, Nov. 30, 1981, abandoned.

[30] Foreign Application Priority Data

Nov. 28, 1980 [GB] United Kingdom ............... 8038282

[51] Int. Cl.$^3$ ............................................. B01D 15/00
[52] U.S. Cl. ....................................... 210/689; 568/916
[58] Field of Search ....................... 210/689; 546/353; 549/429; 568/410, 916, 917

[56] References Cited

U.S. PATENT DOCUMENTS

3,398,208 8/1968 Ward ................................. 210/689
4,130,484 12/1978 Marwil et al. ..................... 210/689

FOREIGN PATENT DOCUMENTS

1111943 5/1968 United Kingdom .
1193127 5/1970 United Kingdom .

Primary Examiner—Ivars C. Cintins
Attorney, Agent, or Firm—Stevens, Davis, Miller & Mosher

[57] ABSTRACT

Organic solvents miscible with water and containing from 2 to 50% of water can be dried by passage over a molecular sieve capable of retaining water after it has been dehydrated, at a superficial velocity of less than 15 cm/min and using columns having specified lengths relative to the mass transfer zone.

4 Claims, No Drawings

TREATMENT OF ORGANICS CONTAINING WATER

This application is a continuation of application Ser. No. 325,902, filed Nov. 30, 1981, now abandoned.

This invention concerns the treatment of organics containing water, and more particularly concerns the removal of water from organic solvents.

The treatment of organic solvents containing from a few ppm up to 1% of water by passage through a column containing a molecular sieve, is known and is industrially practised. Waste solvents are thus dried to very low water contents and upgraded. The organic solvents treated are those miscible with water and they contain substituents such as oxygen, halogens, nitrogen and include certain sulphur-containing compounds.

The value of organic solvents containing more than 1% water very much reduced and, depending upon the water content, they are distilled to a low water content at which they can be treated with a molecular sieve (subject to azeotrope formation) or they are used as low grade solvents, as fuel or even discarded completely.

It has been proposed, in U.K. Pat. No. 1,193,127 (equivalent to French Pat. No. 1,542,755) to dehydrate industrial solvents using powdered molecular sieves with certain specified particle size and attrition index properties. An example is given of the dehydration of ethanol containing 4% water, the ethanol-water azeotrope. This patent does not concern itself with the superficial velocity of the solvent over the molecular sieve, and it recommends the use of a moving bed sieve in which a portion of the sieve is continuously removed and regenerated. Details are given of the velocity of the regenerating gases but not, as has been said, of the velocity of the solvent to be tested; it is only stated that the liquid contact time should be "sufficient" to provide the desired degree of drying.

U.K. Pat. No. 1,111,943 (equivalent to French Pat. No. 1,442,418) also proposes that a certain activated naturally-occuring molecular sieve can be used to dehydrate organic solvents, and gives better results than other commercial sieves, including Linde (Registered Trade Mark) Type 4A, particularly with regard to exhaustion values. Examples are given of the dehydration of ethanol containing 0.5% water and toluene containing 0.052% water.

It is an aim of the present invention to dry organic solvents containing relatively large amounts of water. In particular, it is an aim to provide a process using molecular sieves in which an adequate capacity of the sieve for water can be utilised and which hence does not require continuous regeneration or a very short time between regenerations, which we believe to be the case with any prior proposed process.

The present inventors have discovered that the previously held beliefs in the molecular sieve industry that the capacity of any sieve for water is low (in the examples of U.K. Pat. No. 1,111,943 capacities of 4 to 6% are observed) and that the capacity of the sieve for water is not dependent upon the water content of the feed, are not accurate. That is, it has been found that, by adjusting the superficial velocity of high water-content solvents, a short mass transfer zone can be achieved, and also the usable capacity of the sieve for water surprisingly is substantially increased with several attendant advantages.

Accordingly, the present invention provides a method of drying an organic solvent miscible with water and containing from 2 to 50% by weight, preferably 4 to 25% by weight, of water, comprising passing the solvent through a column containing a dehydrated molecular sieve, at a superficial velocity of less than 15 cm/min and wherein the ratio of the column length to the mass transfer zone defined as the volume of liquid at between 5 and 30% by weight of the feed water content passing through the column divided by the cross-sectional area of the apparatus is at least 4 to 1.

The solvent is advantageously an alcohol, a ketone, an aldehyde, an ester or glycol or chlorine-substituted derivative, or an ether such as tetrahydrofuran providing it is miscible with water. The present invention is especially useful for the treatment of solvents which form azeotropes with water. A particular example is the removal of water from a 4% ethanol binary azeotrope, for example in the production of synthetic fuels by the route termed "biomass". The solvent need not be pure but could be a blend of compounds.

Previously, manufacturers of molecular sieves recommended superficial velocities for the drying or organics of a minimum of 30 cm/min up to about 300 cm/min, whereas particularly suitable superficial velocities in the present invention are from 0.25 to 7.5 cm/min. Experimental work has shown that not only does the invention provide a method of reducing the water content of solvents from what was previously regarded as very high levels to about 0.1% by weight, but also these very low superficial velocities at least double the useful capacity of the molecular sieve, and thus in the method of the invention the mass transfer zone for transfer of water from the solvent to the molecular sieve is found to be short; this enables optimisation of the design of columns which contain the molecular sieves, within quite wide variations in diameter to length ratios, leading to advantages in the construction of plant.

The molecular sieves for use in the present invention are conveniently the zeolites having an A-type crystal structure, for example those zeolites marketed under the designations A3, A4 and A5. referably an A3 zeolite is used.

The method of the invention is suitably carried out under ambient conditions of temperature and pressure, but may, if required, be carried out at elevated or reduced temperature or pressure.

For example, certain materials can be degraded when passing through a molecular sieve. The heat of absorption of water produced in the narrow mass transfer zones found in the present invention can lead to quite high temperatures, sometimes close to the boiling temperature of the solvent being processed. Furthermore, molecular sieves may catalyse decomposition because of their large surface areas and other characteristics. Tetrahydrofuran, for example, suffers from degradation in the method of the invention, but it has been found that cooling the column to maintain the temperature in the mass transfer zone to below 50° C., preferably below 30° C., is effective to reduce this effect. Cooling may be achieved by having a cooling water or forced air jacket around the column, and good results have also been achieved by dilution of the molecular sieve with an inert material, for example sand, arranged in alternate layers within the sieve or dispersed throughout the sieve.

If desired, the product of the method of the invention can be dried further, that is "polished", by passage at conventional rates through a further column, which is suitably a type A zeolite, especially a type A3 zeolite.

The molecular sieve may be regenerated in conventional manner, by passing a hot gas through the column.

The present invention will now be illustrated by reference to the following Example.

EXAMPLE

Isopropanol containing 12.1% by wt. water was passed upwards through a conventional column containing a 1175 g bed of a type A3 molecular sieve at a superficial velocity of 5.1 cm/min, at ambient temperature and pressure. The product was isopropanol containing 0.1% by wt. of water. The ratio of column length to mass transfer zone was approximately 13:1.

If the feed was passed through the column at the minimum rate recommended by the manufacturers of the molecular sieves, namely 30 cm/min, it was found impossible to reduce the water content of the accumulated product below 1% by wt, and the usable capacity of the sieve was only half that when using the present invention (16%). In the example of the invention, 2000 ml of solvent product were obtained before the water content of the product exceeded 0.1%.

Columns of a variety of dimensions up to and including pilot plant size, but all having a column length to mass transfer zone lengths (for the various solvents treated) of greater than 10:1 and usually 13:1, were filled with commercial type A3 molecular sieves. The following solvents were each passed through a column, at a superficial velocity of 5 cm/sec:

Industrial Methylated Spirit (IMS, having an approximately 95:5 ethanol:methanol ratio) and containing various water contents from 4 to 10% by wt. of water;
  Ethyl acetate containing 3.1% by wt. of water;
  Ethanol containing 4 to 15% by wt. of water;
  Methyl Isobutyl Ketone containing 3 to 5% water by wt;
  Acetone containing 15% water by wt;
  Pyridine containing 23% water by wt;
  Tetrahydrofuran containing 3.4 to 10% water by wt.

All the solvents were dried to water contents of less than 0.1% by weight in a single pass; the product pyridine contained less than 0.01% by weight of water.

The method of the invention has been found to give excellent results in a particularly cost-effective manner for the drying of a wide variety of hitherto low-value or difficult to handle solvents. The control by the invention of the size of the mass transfer zone gives an excellent capacity for water, frequently five or six times that shown by published prior art processes.

We claim:

1. In the method of drying an organic solvent miscible with water to a water content of at most 0.1% by weight by passing the solvent through a column containing a dehydrated molecular sieve, the improvement comprising treating a solvent selected from the group consisting of isopropanol, ethanol, industrial methylated spirit, methyl isobutyl ketone, acetone, tetrahydrofuran and pyridine containing from 4 to 25% by weight of water at a superficial velocity of from 0.25 to 7.5 cm/min in a column having a ratio of length to mass transfer zone defined as the volume of liquid at between 5 and 30% by weight of the feed water content passing through the column divided by the cross-sectional area of the column of at least 4 to 1.

2. The method of claim 1, wherein the ratio of column length to mass transfer zone is at least 10 to 1.

3. The method of claim 1, wherein the molecular sieve is a type A3 zeolite.

4. The method of claim 1 wherein the water content of the solvent is 4–15% by weight and the solvent is ethanol.

* * * * *